(12) United States Patent
Bleau

(10) Patent No.: US 7,275,819 B2
(45) Date of Patent: *Oct. 2, 2007

(54) EYEWEAR

(75) Inventor: Michael James Bleau, Grand Blanc, MI (US)

(73) Assignee: SharkLids Eyegear, LLC, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/761,793

(22) Filed: Jan. 20, 2004

(65) Prior Publication Data

US 2004/0218140 A1   Nov. 4, 2004

Related U.S. Application Data

(63) Continuation-in-part of application No. 10/205,238, filed on Jul. 25, 2002, now Pat. No. 6,984,037.

(51) Int. Cl.
*G02C 1/00* (2006.01)

(52) U.S. Cl. .......................... 351/41; 351/111

(58) Field of Classification Search ................. 351/41, 351/154, 86, 83, 111
See application file for complete search history.

(56) References Cited

U.S. PATENT DOCUMENTS

| | | | |
|---|---|---|---|
| 583,590 A | 6/1897 | Bennett |
| 2,149,514 A | 3/1939 | Fischer |
| 2,243,982 A | 6/1941 | Seeley |
| 2,387,851 A | 10/1945 | Lonn et al. |
| 2,430,881 A | 11/1947 | Lehmberg |
| 3,092,103 A | 6/1963 | Mower |
| 3,614,216 A | 10/1971 | Rosenthal |
| 3,701,592 A | 10/1972 | Fernandez |
| 4,006,974 A | 2/1977 | Resnick |
| 4,122,847 A | 10/1978 | Craig |
| 4,393,080 A | 7/1983 | Pawelchak et al. |
| 4,547,909 A | 10/1985 | Bell |
| 4,797,956 A | 1/1989 | Boyce |
| 4,837,862 A | 6/1989 | Heil |
| 4,886,349 A | 12/1989 | Willis |
| 4,944,294 A | 7/1990 | Borek, Jr. |
| 5,016,999 A | 5/1991 | Williams |
| 5,020,533 A | 6/1991 | Hubbard et al. |
| 5,302,977 A | 4/1994 | Markovitz et al. |
| 5,383,450 A | 1/1995 | Hubbard et al. |
| 5,406,944 A | 4/1995 | Gazzara |
| 5,419,913 A | 5/1995 | Podell et al. |

(Continued)

FOREIGN PATENT DOCUMENTS

JP   11 128378   5/1999

(Continued)

*Primary Examiner*—Hung Xuan Dang
(74) *Attorney, Agent, or Firm*—Goodwin Procter LLP

(57) ABSTRACT

Novel eyewear are disclosed which comprise a lens and a sealing frame. The lens is adapted to cover at least one of a user's eyes. The frame has an adhesive side and is disposed adjacent the perimeter of the lens. A first portion of the adhesive side is disposed at the perimeter of the lens forming a seal between the frame and the lens. A second portion of the adhesive side extends laterally beyond the perimeter of said lens to provide adhesive attachment of the eyewear to the face of the user.

20 Claims, 13 Drawing Sheets

U.S. PATENT DOCUMENTS

| | | |
|---|---|---|
| 5,425,380 A | 6/1995 | Hudson et al. |
| 5,584,078 A | 12/1996 | Saboory |
| 5,700,238 A | 12/1997 | Hyson |
| 5,719,655 A | 2/1998 | Peschel et al. |
| 5,797,146 A | 8/1998 | Matich |
| 5,949,514 A * | 9/1999 | Wargon ................. 351/41 |
| 6,019,103 A | 2/2000 | Carroll |
| 6,026,511 A | 2/2000 | Baumann et al. |
| 6,196,223 B1 | 3/2001 | Belfer et al. |
| 6,216,695 B1 | 4/2001 | Ruben |
| 6,526,975 B1 | 3/2003 | Chung |
| 6,543,450 B1 | 4/2003 | Flynn |
| 6,609,516 B2 | 8/2003 | Hollander et al. |
| 6,761,447 B1 | 7/2004 | Pyo |
| 6,776,485 B2 | 8/2004 | Cole |
| 6,984,037 B2 * | 1/2006 | Bleau ................. 351/83 |

FOREIGN PATENT DOCUMENTS

| | | |
|---|---|---|
| WO | WO97/21397 | 6/1997 |
| WO | WO 02/06881 | 1/2002 |

* cited by examiner

EYEWEAR

RELATED APPLICATIONS

This application is a continuation-in-part of application Ser. No. 10/205,238, filed Jul. 25, 2002 now U.S. Pat. No. 6,984,037.

FIELD OF THE INVENTION

The invention relates to eyewear, specifically to goggles and eye shields that provide protection and/or vision enhancement, particularly where a closely conforming, flexible material contacts the area surrounding the eye for the purpose of sealing a lens or shield against the wearer's face for activities such as swimming. The eyewear can also be used in medical applications for protection against exposure to body fluids, or in recreational applications such as sunglasses.

BACKGROUND OF THE INVENTION

Goggles are commonly used to keep a user's eyes isolated from the surrounding atmosphere. For example, swimming goggles are utilized to protect the eyes from water. Other goggles, such as protective goggles, prevent exposure of the user's eyes to toxins or contaminated material, such as blood or eye irritants. Goggles may also be used to protect the eyes from harmful or undesirable environmental conditions, such as cold or dry air or sand or dust in the air. Goggles may also be used to retain a particular fluid or gas in contact with the user's eyes or face.

Generally speaking, eye goggle designs employ soft, spongy material between the area surrounding a user's eyes and the perimeter of the goggle lens and a head strap to hold the goggles in place against the wearer's face. For example, traditional swimming goggles seal each eyepiece or lens against the face in a water tight manner by the elastic force of a head strap pulling the eyepiece against the face, and suction forces created during the fitting of the goggles onto the user's face, leaving negative pressure inside the eyepiece.

It is well known in the art that these forces create pressure points and a certain amount of discomfort in exchange for a water-tight fit. Greater forces generally impart greater discomfort, but also a more secure fit against leakage.

Traditional, strap-type swimming goggles can slip off of the wearer's face during diving or flip-turns where the wearer is moving at higher velocity through the water than when simply swimming. It would be desirable to have goggles that provide a more secure fit and a low profile to reduce drag and that will remain in place on the user's face. In medical applications, the wearer being an EMT, surgeon or other type of health care provider, would benefit from a disposable, inexpensive eye shield that not only protects the wearer from fluid exposure, but also the patient from possible contamination of sweat dripping from the health care worker onto or into the patient.

Thus, it is desirable to develop a goggle design that provides a substantially water-tight seal for a user's eyes that eliminates or reduces the need for straps or elastic bands or requirements for additional forces to retain the goggles in place over the user's eyes.

It is also desirable to develop a face or eye shield design that provides isolation of a user's eyes or face that eliminates or reduces the need for straps or elastic bands or the requirement for additional forces to retain the face or eye shield in place over the user's face or eyes.

SUMMARY OF THE INVENTION

An object of this invention is to provide an economical yet precisely made, preferably optically clear eyewear such as goggles which extends broadly the range of comfortable fit for a user requiring closely conforming eye protection.

The present invention provides eyewear for protection of a user's eyes and isolation thereof from the outside environment. The eyewear generally comprises two components, namely a lens and a sealing frame. The lens is adapted to cover at least one of a user's eyes. The sealing frame has an adhesive side, which is disposed along the perimeter of said lens. A first portion of the sealing frame adhesive side is disposed at the perimeter of said lens forming a substantially airtight or watertight seal between said frame and said lens. A second portion of sealing frame adhesive side extends from said first portion laterally beyond the perimeter of said lens. The second portion provides a means for forming a substantially airtight or watertight seal between the sealing frame and at least a portion of the user's face adjacent the perimeter of said lens.

In a preferred embodiment, the interior side of the lens has a fog resistant coating. In another preferred embodiment, the lens has UV protection incorporated therein or thereon. The exterior side of the lens may optionally have a water-shedding coating.

DETAILED DESCRIPTION OF PREFERRED EMBODIMENTS

Figure 1:
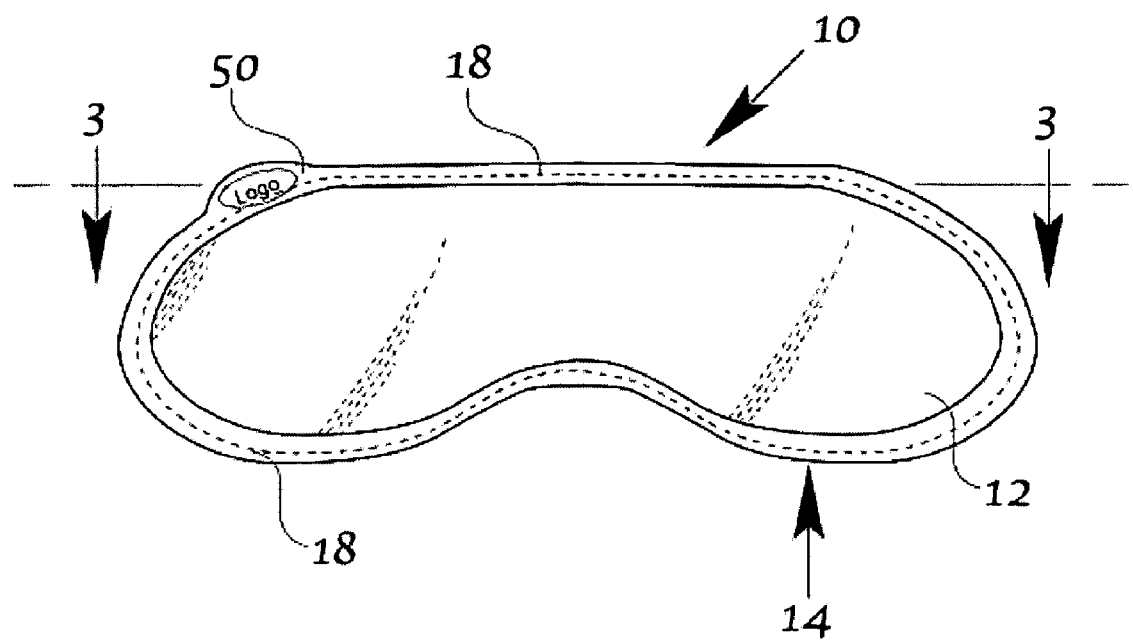
FIG. 1 is a top plan view of eyewear according to the present invention.
Figure 2:
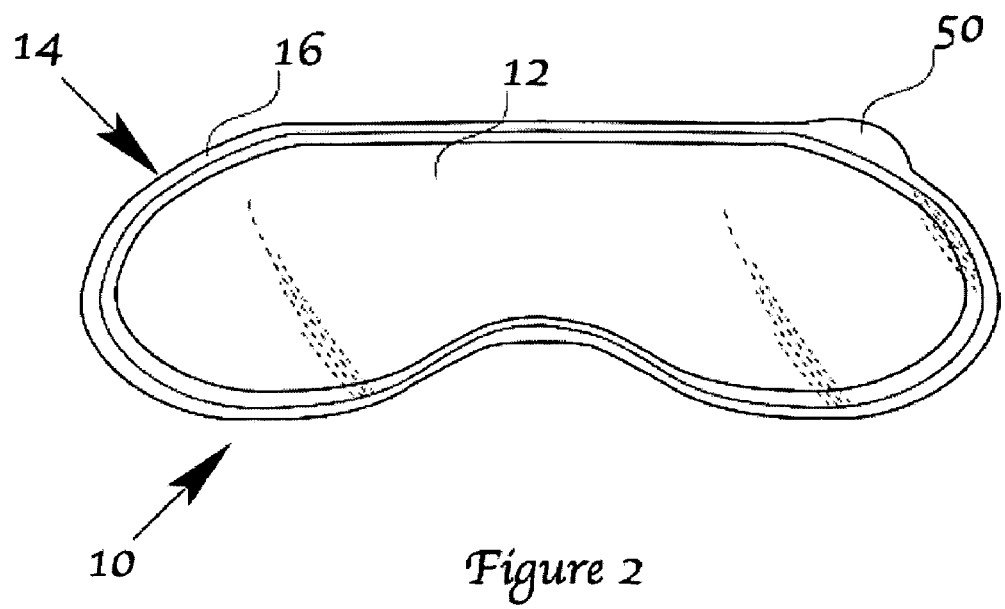
FIG. 2 is a bottom plan view of eyewear according to the present invention.

FIGS. 1 and 2 show eyewear 10 in accordance with the present invention. Eyewear 10 generally provides protection to the eyes of a user during use by isolating the user's eyes from the outside environment. In an alternative embodiment, this eyewear can be used to retain a particular fluid or gas in contact with the user's eyes or face.

The eyewear 10 generally comprises two components, namely a lens 12 and a frame 14. The lens 12 is adapted to cover at least one of a user's eyes. At least a portion, and preferably the entire lens 12 is transparent. In an alternative embodiment, however, the lens is opaque, thereby preventing all visible light from passing through the lens to the user's eyes. The lens material may be flexible, semi-rigid or rigid in nature. If the lens material is semi-rigid or rigid, the contour of the lens should generally conform to the shape and contours of the user's face. This is particularly desirable around the user's eyes to accommodate the user's eyes behind the lens and away from the environment from which protection is desirable. The lens material, however, is flexible in nature, thereby allowing the lens 12 to conform to the shape and contours of a user's face around the user's eyes. This provides for greater freedom from a manufacturing perspective to the extent that a uniform lens can be manufactured from a flexible material for a segment of user's, thereby averting the need to customize the lens for each user since the lens will conform to the contours of user's face during application of the eyewear onto the user's face.

Suitable materials for the lens include polyvinyl chloride (PVC), acrylics, polyester film, such as Mylar (commercially available from Dupont), and polystyrene including general-purpose polystyrene and high impact polystyrene. The lens material can be virtually any type of material that can be designed to fit and generally conform to the shape of the user's face and around the user's eye socket. The lens material is preferably a transparent, plastic material. In one embodiment, the material is a thin film of transparent, flexible plastic material that is sized such that the perimeter of the lens runs along the contours of the user's face beyond the user's eye sockets to fit outside the user's orbit.

Other suitable lens materials include those with reflective surfaces and UV filtering properties, including materials for sunglass embodiments from CP Films, Inc. (Martinsville, Va.), including those from the Halcyon™ Shades product line that makes use of LLUMAR® Technology. Llumar® Window Film is a micro thin film composed of polyester and metallized coatings bonded by adhesives that is installed onto glass surfaces to provide significant solar protection. Such materials screen out heat, block out 99% of the sun's damaging ultraviolet rays and deflect harsh, uncomfortable glare while allowing glare-controlled sunlight to pass through. Llumar adapts to the changes in the seasons, reflecting the hot sun in the summer, and with Low-E films to reradiate heat in the winter, the user can be comfortable all year long. Llumar is ruggedly constructed and resists scratching.

In a preferred embodiment of the invention, lens material comprises a clear plastic material such as 2 mil thick polystyrene. The lens material may be coated to resist fogging as well as protect against UV penetration. Also, the exterior of the lens preferably has a water-shedding coating, which is particularly useful in an embodiment for use as a swim goggle.

The frame 14 of the eyewear 10 has an adhesive side 16, which is disposed adjacent or runs generally along the perimeter 18 of the lens 12. A first portion of the frame adhesive side is disposed at the perimeter of said lens forming a substantially airtight or watertight seal between said frame and said lens. A second portion of sealing frame adhesive side extends from said first portion laterally beyond the perimeter of said lens. The second portion provides a means for forming a substantially airtight or watertight seal between the sealing frame and at least a portion of the user's face adjacent the perimeter of said lens.

Suitable material for the frame 14 is a flexible, compliant, preferably elastic material that will conform to the contours of the user's face. The frame material will have an adhesive characteristic on at least the portion defining the adhesive side 16. Thus, the frame may comprise flexible, compliant adhesive material which possesses the desirable adhesive properties or may comprise flexible, compliant material to which has been applied an adhesive substance providing the adhesive properties. Such materials are well known in the art.

In a preferred embodiment of the invention, the frame material comprises a hypoallergenic material such as 3M Corporation's Medical Specialties Health care division's product number 1526, being a 3.6 mil thick, transparent, polyethylene film, coated on one side with a hypoallergenic pressure sensitive acrylate adhesive. The tape is supplied on a polyethylene-coated, bleached Kraft paper liner, with a basis weight of 63 pounds, silicone coated one side, which has a nominal caliper of 4.9 mil. According to 3M product clinical data summaries for safety testing, the 1526 material has been subjected to the safety tests that provide adequate hypoallergenic properties.

Other suitable frame materials include 3M Plastic Medical Tape, product number 1521, which is a single coated medical tape consisting of a 5 mil, transparent polyethylene film, coated on one side with a hypoallergenic, pressure sensitive acrylate adhesive. The tape is supplied on a polyethylene coated, bleached Kraft paper liner, with a base weight of 83 pounds, silicone coated one side, which has a nominal caliper of 6 mils (0.15 mm). Product properties include: Minimum adhesion to steel at 512 g/25 mm and a maximum of 938 g/25 mm. Other frame material properties may include an adhesive component that is impregnated with perspiration retarding elements that will prolong the useful life of the adhesive during aggressive activities (i.e. marathon running).

Figure 3:
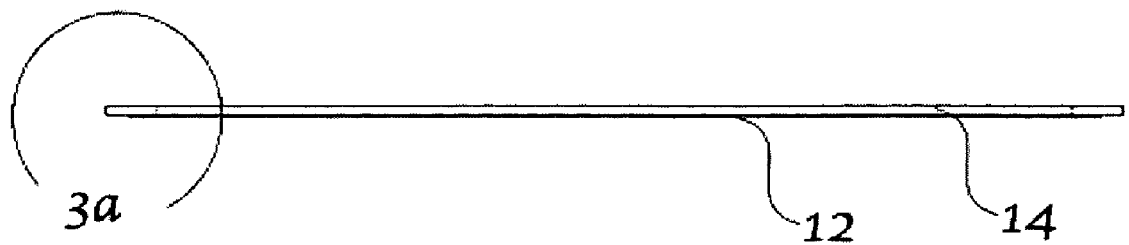
FIG. 3 is a cross-sectional view of eyewear according to the present invention along line 3-3 of FIG. 1.
Figure 3A:
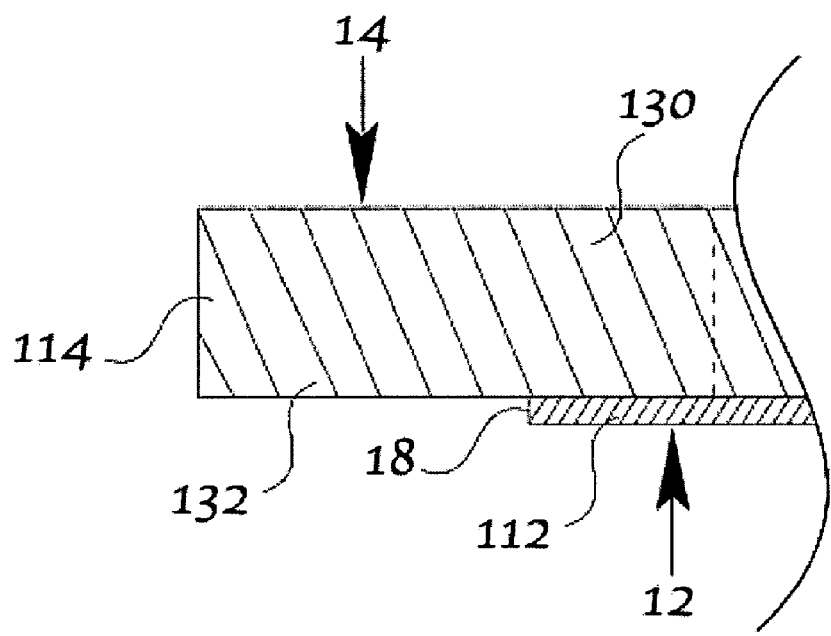
FIG. 3*a* is a partial, magnified cross section of an end of the eyewear in FIG. 3.

In FIGS. 3 and 3a, frame 14 is shown disposed adjacent lens 12 and adhesively attached thereto particularly along perimeter 18 of lens 12. As seen in FIG. 3a, frame end 114 overlays lens end 112 such that the frame end 114 extends beyond perimeter 18 of lens 12. As described previously, frame 14 has an adhesive side that provides assembly of the eyewear 10 along a first portion 130 of frame 14. Further, the adhesive side 16 of frame 14 provides a means of adhesive attachment to the face of a user, preferably in a releasable manner, along a second portion 132 of frame 14. Although the construction of the eyewear is illustrated herein as provided by adhesive attachment between the frame and lens, any means of attachment between the frame and lens in the first portion of the frame that is known in the art can be utilized for such construction. This would include laser bonding, melt bonding or pressure bonding. Irrespective of the means of construction, the frame should have an adhesive or tacky material along the second portion thereof to provide preferably releasable attachment to a wearer's face.

In a preferred embodiment of the invention, the frame material comprises a hypoallergenic material such as 3M Corporation's Medical Specialties Health care division's product number 1526 provides release from the wearer's face with little or no discomfort. According to 3M product testing, the 1526 material exhibits the following material properties:

| (1) Adhesion to steel: | Minimum 850 g/25 mm 30 oz/in (8.33 N/25 mm) |
|---|---|
| (2) Liner release: | Maximum 50 g (0.49 N)/25 mm |
| (3) Tape caliper w/o liner: | 5.0 mils ± 1.0 mil |

(4) Product as specified above in 1-3 as supplied in original packaging, will maintain stated test properties for a period of 2 years, when stored at a temperature between 50-80 degrees F. and a relative humidity between 40-60 percent.

Figure 4:
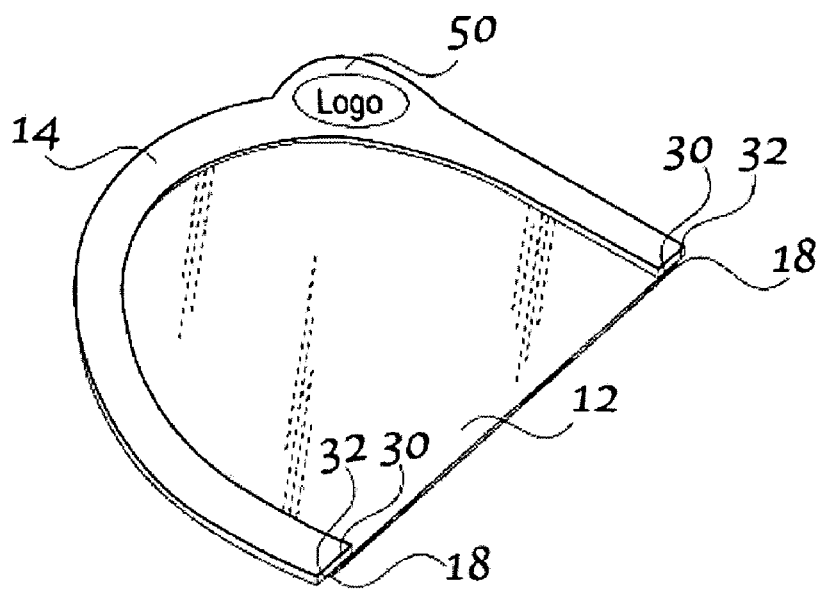
FIG. 4 is a perspective view of eyewear according to the present invention in cross section.

In FIG. 4 is shown again lens 12 and frame 14 which generally make up the novel eyewear of the present invention. Frame 14 overlays lens 12 where adhesive side of the frame 14 is attached or secured to lens 12 at first portion 30 and partially exposed at second portion 32 to secure to a user's face. Frame 14 generally runs along perimeter 18 of lens 12. In addition to providing adhesive means for preferably releasable attachment to a user's face, second portion 32 provides for releasable attachment to a backing layer prior to usage by a user. During assembly of the eyewear 10, and also afterwards during storage, second portion 32 of frame 14 provides releasable attachment to a material such as a backing layer.

Tab 50 is an appendage upon which can be placed a logo or other identifying indicia. Tab 50 provides more importantly a portion of frame 40 from which a user can grasp to remove the eyewear assembly from the backing layer used during storage or from the user's face once the user is done using the eyewear and wants to dispose of the eyewear. Thus, tab 50 provides for easy removal from backing paper and for placement of insignia or logo.

Figure 5:
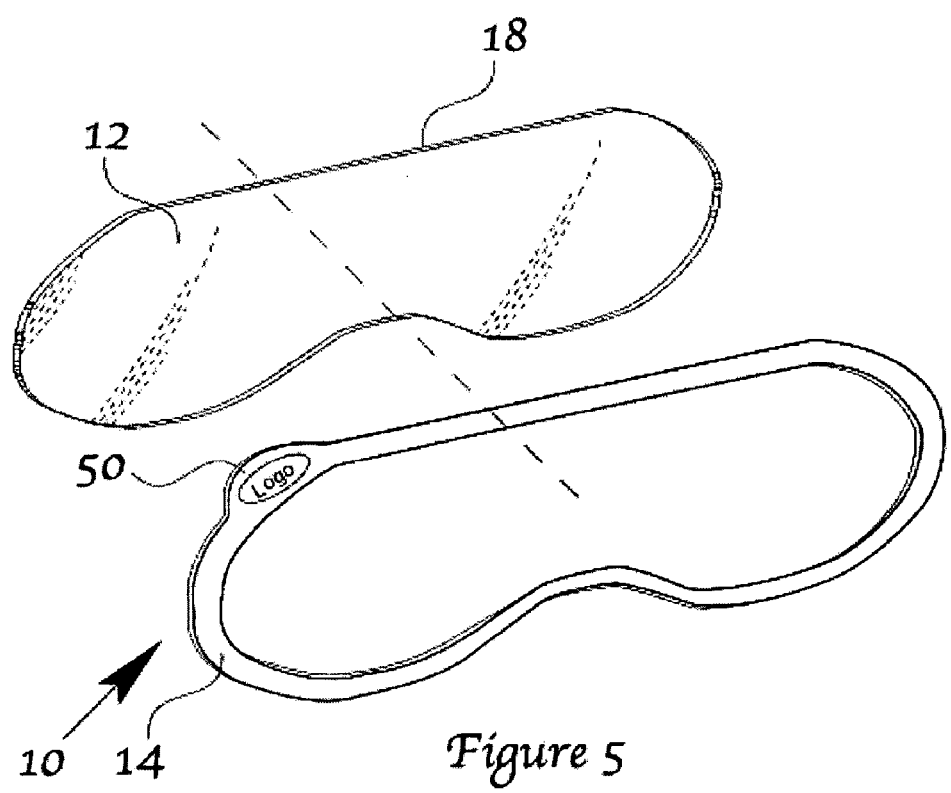
FIG. 5 is an exploded view of eyewear according to the present invention

FIG. 5 generally shows the construction of eyewear 10. Eyewear 10 generally comprises a two-piece construction comprising lens 12 and frame 14, where frame 14 overlays lens 12 generally along the perimeter 18 of lens 12. As described previously, a first portion 30 provides substantially airtight or watertight seal to lens 12 and second portion 32 extends beyond perimeter 18 of lens 12.

Figure 6:
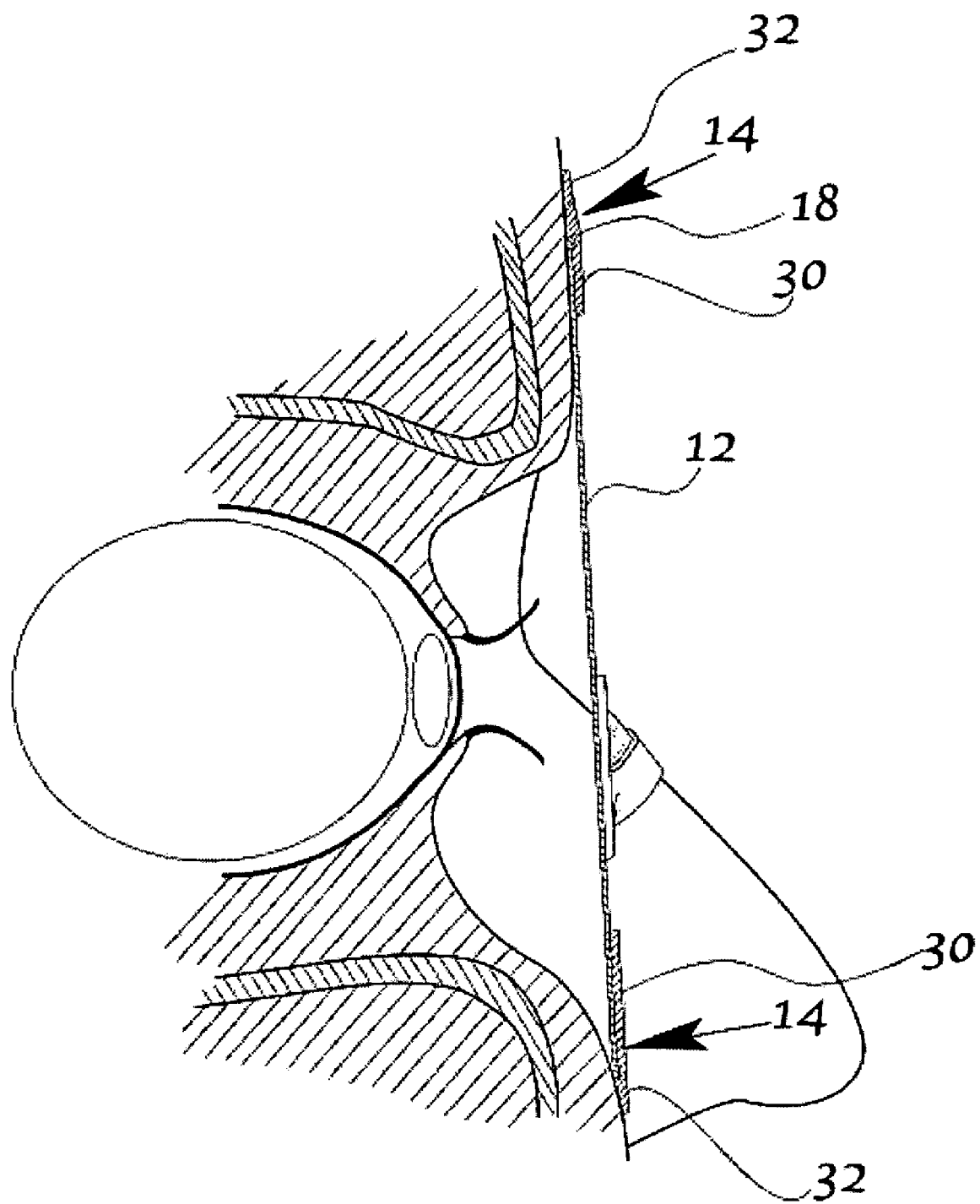
FIG. 6 is a pictorial cross section of eyewear according to the present invention as worn by a user.

FIG. 6 shows the eyewear 10 in use. Lens 12 covers a wearer's eye. Frame 14 comprising first portion 30 and second portion 32 runs along perimeter 18 of lens 12. First portion 30 provides suitable attachment of frame 14 to lens 12 while second portion 32 extend beyond perimeter 18 and preferably beyond any facial hair of the wearer such as the eyebrows to secure the eyewear to wearer's skin in a releasable fashion. FIG. 6 also illustrates how frame 14 follows the contours of the wearer's face particularly along the bridge of the nose.

Figure 7:
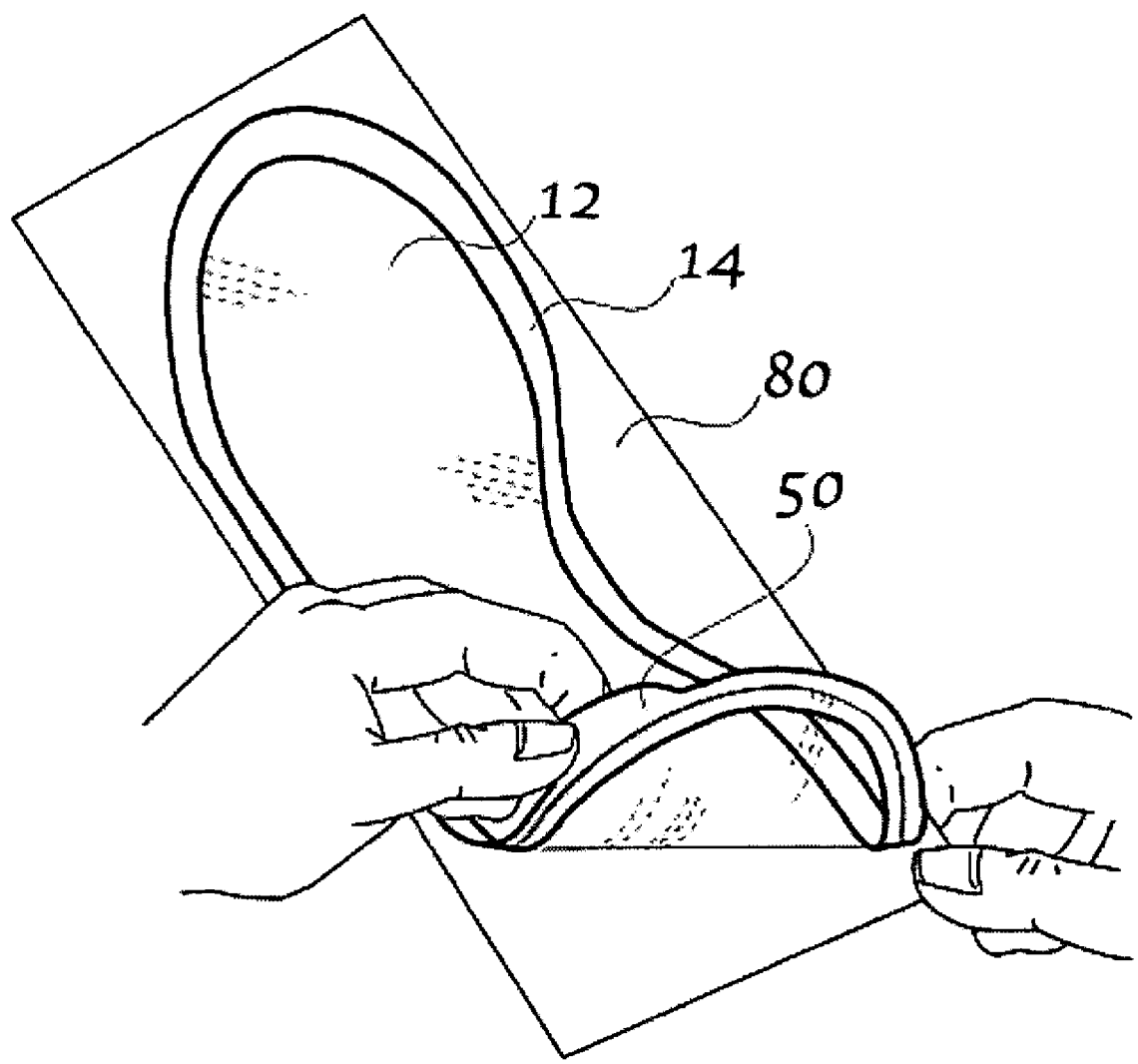
FIG. 7 is an illustrative view of eyewear according to the present invention as partially packaged with a backing layer.

FIG. 7 generally illustrates how the eyewear 10 could be packaged for use by a wearer. The eyewear assembly comprising lens 12 and frame 14 can be positioned on a backing layer 80 during storage and transport whereby second portion 32 provides releasable attachment to backing 80. Tab 50 provides an appendage from which a wearer can remove eyewear 10 from backing 80.

Backing 80 can be any suitable material that is complimentary to adhesive side 16 of frame 14 to provide releasable attachment of the eyewear to backing 80. Polyethylene coated, bleached Kraft paper liner, preferably with a basis weight of 63 pounds, silicone coated one side, which has a nominal caliper of 4.9 mil is a suitable material.

The user, after opening the packaging (not shown), removes the assembled eyewear 10 and applies it directly to their face, covering their eyes.

Figure 8:
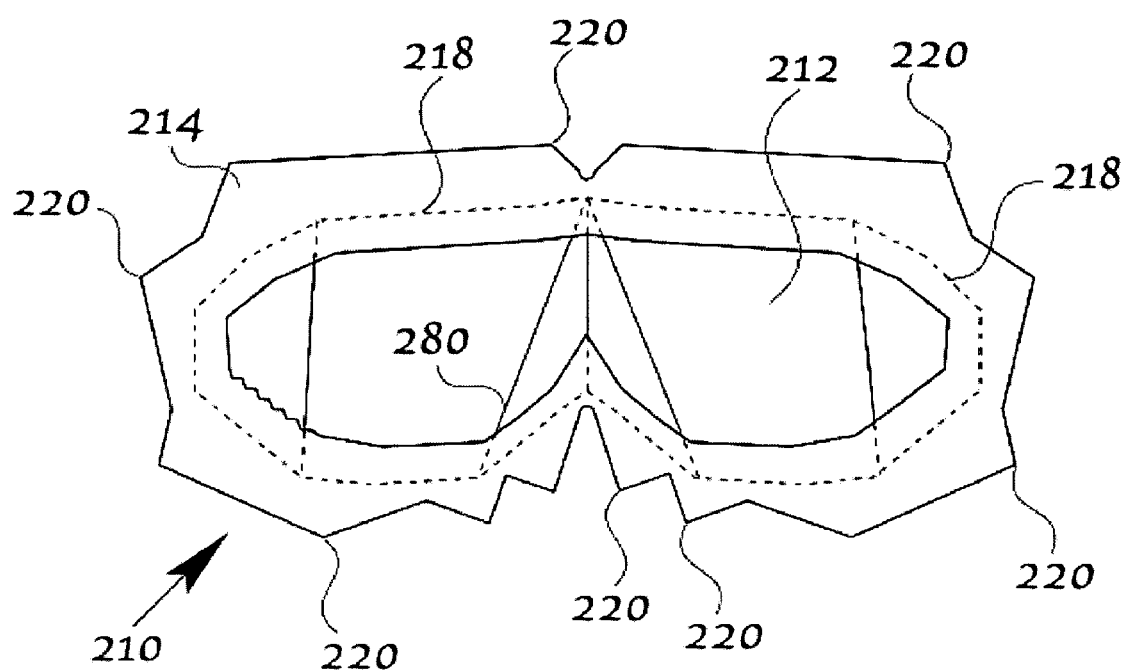
FIG. 8 is a top plan view of an alternative embodiment of eyewear according to the present invention.

FIG. 8 illustrates an alternative embodiment of the novel eyewear. Eyewear 210 comprises frame 214 and lens 212 having a perimeter 218. Frame 214 has a plurality of notches 220 that provide better arrangement of the eyewear around the contours of a user's face. The geometry of the frame 214 allows for easier manufacturing of the eyewear 210. For ease of manufacture, eyewear 210 is made of generally flat materials. The generally flat assembly in order to more readily conform to the user's facial structure incorporates a plurality of notches 220 to aid in conforming to the contours of a wearer's face. For example, as the frame 214 and lens 212 conforms to the contours of a wearer's face around the nose of the wearer, the tips or points of the facets at the nose area move closer together as they follow the projected curvature of the nose. Without the facets, lens 214 would buckle, folding onto itself, creating the potential for leaks as well as increasing drag against water in competitive swimming events. Just as in previous embodiments, frame 214 runs along perimeter 218 of lens 212.

Frame 214 is adhered to lens 212 adjacent the perimeter 218 of lens 212 along a first portion of the adhesive side of frame 214. A second portion of the adhesive side of frame 214 is adapted to adhere to the face of the user, generally around the contours of the user's face around the eyes. To further facilitate the fit of the eyewear 210 on a user's face, lens 212 preferably has scoring 280 that run vertically along the lens material, typically on the outer surface of the lens 218. Scoring 280 can also run horizontally or diagonally. Such scoring is known in the art and can be generally characterized as cuts or etchings in the lens material that assist or facilitate the bending of the lens along such cut or etching, thereby helping the lens 212 conform to the contours of the user's face. Scorings 280 also allow the user to bend or crease the lens material along such scorings to provide a better fit on the user's face.

Figure 9:
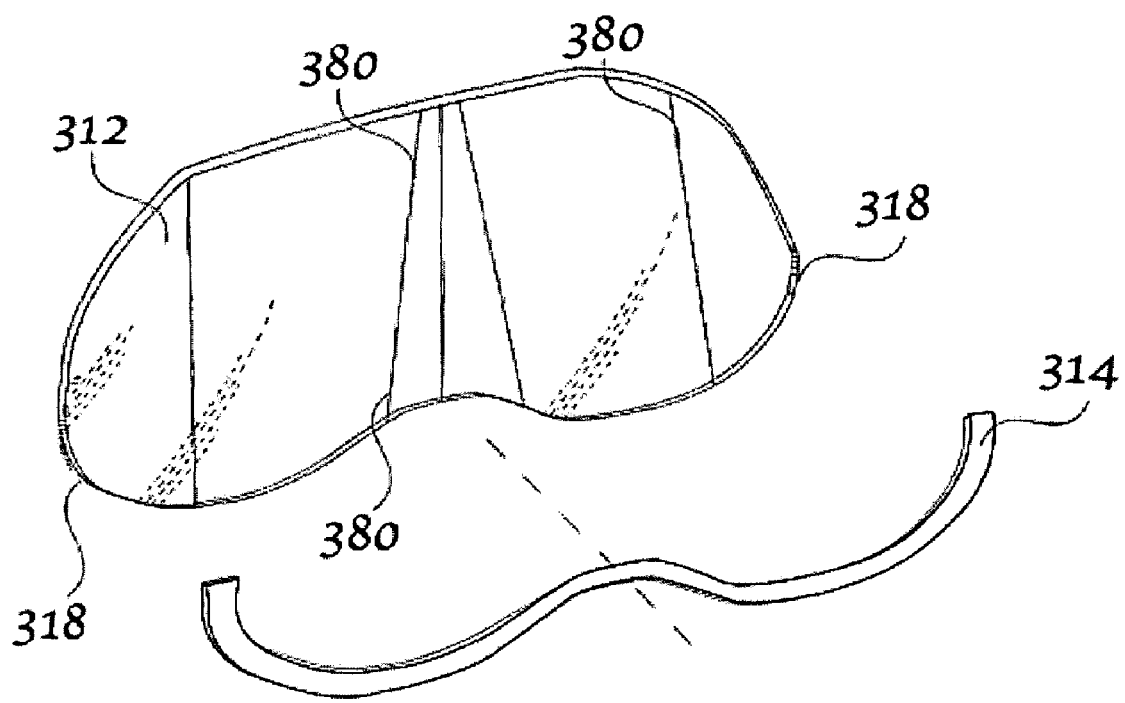
FIG. 9 an exploded view of an alternative embodiment of eyewear according to the present invention.

FIG. 9 illustrates an alternative embodiment of the novel eyewear. This alternative embodiment could be useful for medical application as a protective splash shield from bodily fluids. The lens 312 is oversized and extends laterally to the user's temple area and vertically above the brow line. The frame 314 runs along a lower half of the perimeter 318 of lens 312, leaving the upper half of this eyewear embodiment open to the environment. The frame has first and second portions that adhere, respectively, to the lens along the lower half of the lens perimeter 318 and the cheek and nose of the user. This allows for free air movement between the lens 312 and the user's face along the top portion of the alternative embodiment. The free exchange of air ensures that no fog will form on the inside of the lens 312 to ensure maximum visibility for the health care worker. Lens 312 also has scorings 380 that provide better conformity of the eyewear to the contours of the user's face.

Figure 10:
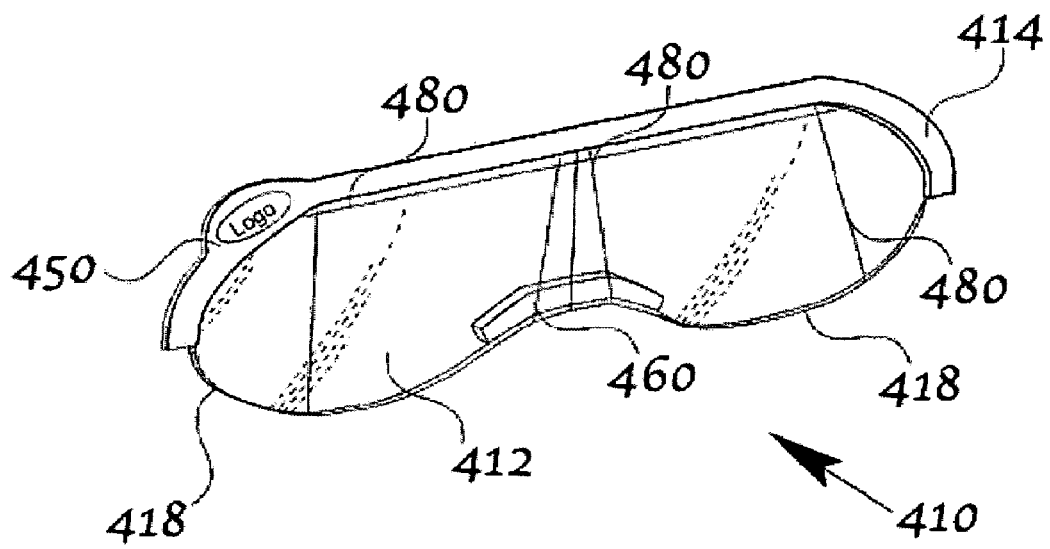
FIG. 10 is a perspective view of an alternative embodiment of eyewear according to the present invention.

FIG. 10 illustrates another alternative embodiment of the novel eyewear. In this alternative embodiment, the eyewear 410 includes lens 412 and frame 414 and further comprises nose pad 460. Frame 414 runs along an upper half of perimeter 418 of lens 412. Nose pad 460 may be any soft material such as a material comprising a ⅛ to ¼ in. thick, high grade, non-toxic, non-skin irritating, vinyl foam material such as Gaska Tape, Inc.'s product MC2010-NA, which provides a cushioned support of the lens 412 and eyewear 410 on the wearer's face along the bridge of the nose. In a preferred embodiment of the alternative invention, the lens 412 material comprises a 5 mil polyester film, such as Dupont's Mylar brand product with UV protective properties and tinting for glare reduction.

Partial frame 414 adheres to the temple and brow line of the user allowing for free air movement between the lens 412 and the user's face along the lower half portion of the alternative embodiment. The free exchange of air helps assure that no fog will form on the inside of the lens 412 to ensure maximum visibility for the user. The seal created along the brow line by the partial frame 414 also ensures that during activity as the user sweats the sweat will be shielded from the eyes and it cannot pass between the frame 414, the lens 412 and the user. Frame 414 includes a tab 450.

Lens 412 also has vertical and horizontal scorings 480. Scorings 480 can be incorporated into the lens material to allow the user to crease the lens 412 for fit adjustment of the eyewear to the user's face. The vertical scorings help conform the lens 412 and eyewear 410 to the contours of the user's face. The horizontal scoring allows the user to bend or flip the eyewear upwards generally along such horizontal scoring. Thus, the user would be able to access the area of their face protected by the eyewear 410 to, for example, wipe sweat from their eyes or apply water or medication without having to remove the eyewear.

Figure 11:
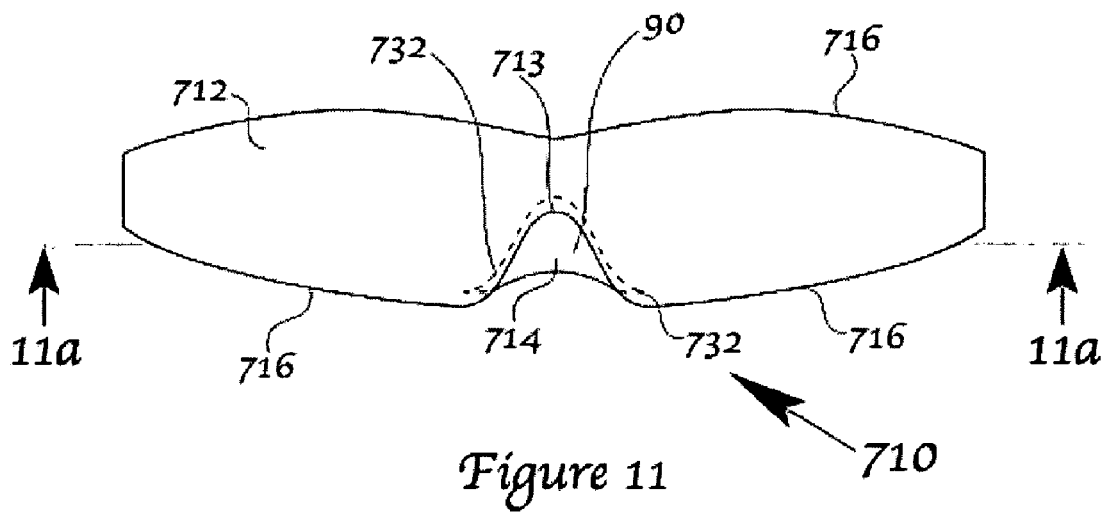
FIG. 11 is a plan view of an alternative embodiment of eyewear according to the present invention.
Figure 11A:
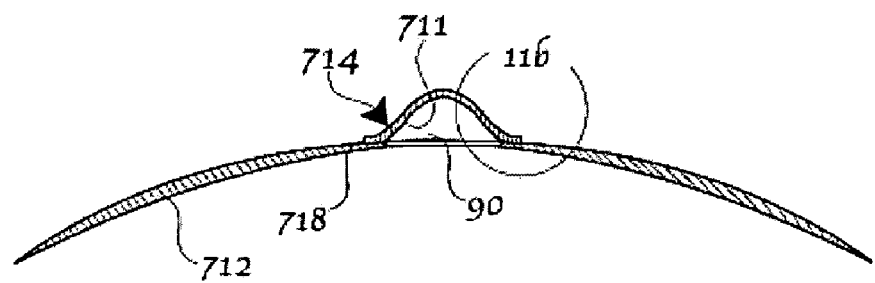
FIG. 11*a* is a cross-sectional view of the eyewear in FIG. 11 along line 11*a*-11*a* of FIG. 11.
Figure 11B:
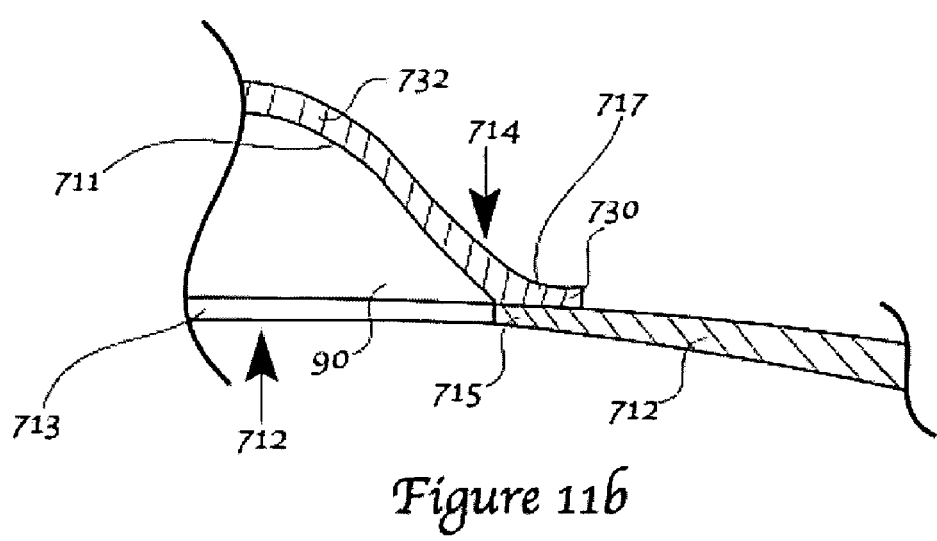
FIG. 11*b* is a partial, magnified cross section of a portion of the eyewear in FIG. 11.

FIGS. 11, 11a and 11b illustrate an alternative embodiment of the novel eyewear. The eyewear 710 generally comprises two components, namely a lens 712 and a frame 714. The lens 712 is adapted to cover at least one of a user's eyes. Lens 712 is preferably transparent. In this embodiment, the lens material is preferably semi-rigid or rigid in nature and the contour of the lens generally conforms to the curvature of the user's face, especially the facial area along which the lens extends during use. This is particularly desirable around the user's eyes to accommodate the user's eyes behind the lens and away from the environment from which protection is desirable. Lens 712 has a perimeter 716. Generally, lens 712 is cut, shaped or molded in such a way so as to protect or shield a desired area of a user's face and along a nose portion 713 in such a way so as to accommodate the user's nose. The shape of lens perimeter 716 along nose portion 713 defines a cutout 90 that is adapted to receive the user's nose.

Frame 714 is adapted to receive a user's nose. Thus, frame 714 has a shape that accommodates a user's nose. Frame 714 also has an adhesive side 711 displaying adhesive characteristics as described above, thereby providing releasable attachment of eyewear 710 to a user's face. A first portion of the adhesive side of frame 714 runs along perimeter nose portion 713. In the illustrated embodiment, an edge of the frame 714 is disposed adjacent or runs generally along the perimeter 716 substantially the length of nose portion 713. A first portion of the frame adhesive side 711 preferably forms a secure attachment between frame 714 and lens 712. A second portion of frame adhesive side 711 extends from said first portion to further define cutout 90 and generally follows the contour of a user's nose. The user's nose occupies cutout 90 during use of eyewear 710. The second portion provides a releasable seal between frame 714 and at least a portion of the user's face adjacent the perimeter of said lens along nose portion 713.

In FIGS. 11a and 11b, frame 714 and lens 712 are shown in adhesive attachment along the perimeter nose portion 713. Frame end 717 overlays lens end 715 adjacent perimeter nose portion 713. As described previously, frame 714 has an adhesive side that provides assembly of the eyewear 710 along a first portion 730 of frame 714. Further, the adhesive side 711 of frame 714 provides a means of adhesive attachment to the face of a user, preferably in a releasable manner, along a second portion 732 of frame 714. Although the construction of the eyewear is illustrated herein as provided by adhesive attachment between the frame and lens, any means of attachment between the frame and lens along the first portion of the frame that is known in the art can be utilized for such construction. This would include laser bonding, melt bonding or pressure bonding. Irrespective of the means of construction, the frame should have an adhesive or tacky material along the second portion thereof to provide preferably releasable attachment to a wearer's face.

In the case of infants and smaller children or during aggressive sports, the adhesive properties of the frame ensures that the eyewear stays in place and provide consistent UV protection, where traditional glasses and goggles can easily fall off during activity. In a medical application for treatment of jaundice in infants using UV light to reduce bilirubin amounts where the lens is opaque to protect the eyes from the sun lamp used to cure such condition.

Figure 12:
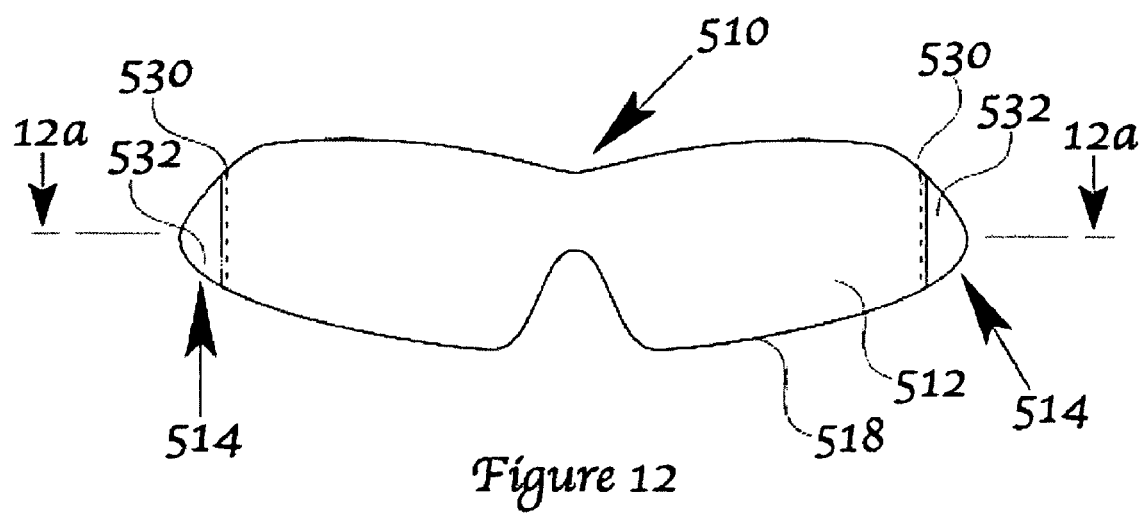
FIG. 12 is a plan view of an alternative embodiment of eyewear according to the present invention.
Figure 12A:
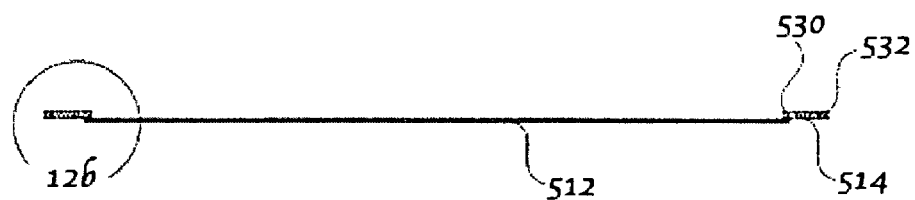
FIG. 12*a* is a cross-sectional view of the eyewear in FIG. 11 along line 12*a*-12*a* of FIG. 12.
Figure 12B:
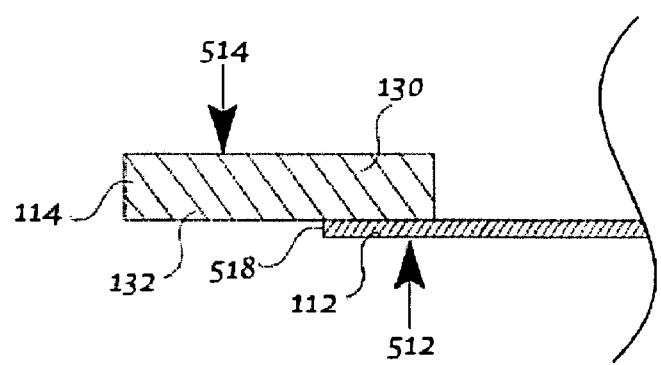
FIG. 12*b* is a partial, magnified cross section of a portion of the eyewear in FIG. 12.

FIGS. 12, 12a and 12b illustrate another embodiment of the present invention where the adhesive frame overlays a portion of the outside diameter of the perimeter along the lateral edges of the lens. The eyewear 510 comprises a lens 512 that extends laterally to cover the user's eyes during use. The eyewear 510 includes two frames 514 disposed at opposed lateral edges of the perimeter 518 of lens 512, which provide adhesive attachment to the lens 512 and a portion of the user's face during use. Depending on the design of this eyewear embodiment, a plurality of frames could be used to provide attachment to the lens and/or the user's face. A substantial portion of this eyewear embodiment remains open to the environment to allow for free passage of air between the lens 512 and the user's eyes. Each frame 514 has a first portion 530 and a second portion 532 that adhere, respectively, to the lens along the lateral edge of the lens perimeter 518 and the lateral portions of the user's face, e.g., adjacent the temple area of a user's face. This allows for free air movement between the lens 512 and the user's face. The free exchange of air ensures that no fog will form on the inside of the lens 512. Lens 512 may include scorings (not shown) that provide better conformity of the eyewear to the contours of the user's face.

As with the embodiment shown in FIG. 10, eyewear 510 in FIG. 12 may further comprises a nose pad (not shown), which provides a cushioned support of the lens 512 on the wearer's face along the bridge of the nose.

In FIG. 12b, frame 514 is shown disposed adjacent lens 512 and adhesively attached thereto along a lateral edge of perimeter 518 of lens 512. As shown in FIG. 12b, frame end 114 overlays lens end 112 such that the frame end 114 extends beyond the lateral edge of perimeter 518 of lens 512. As described previously, frame 514 has an adhesive side that provides assembly of the eyewear 510 along a first portion 130 of frame 514. Further, the adhesive side 516 of frame 514 provides a means of adhesive attachment to the face of a user, preferably in a releasable manner, along a second portion 132 of frame 514. Irrespective of the means of construction of the eyewear, the frame should have an adhesive or tacky material along the second portion thereof to provide preferably releasable attachment to a wearer's face.

Figure 13:
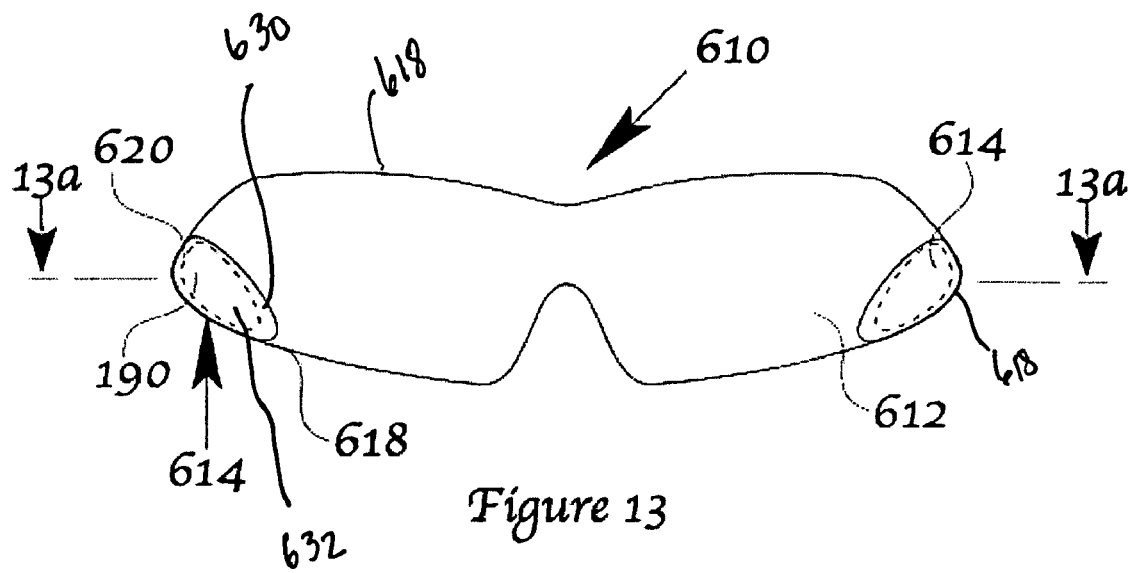
FIG. 13 is a plan view of an alternative embodiment of eyewear according to the present invention.
Figure 13A:
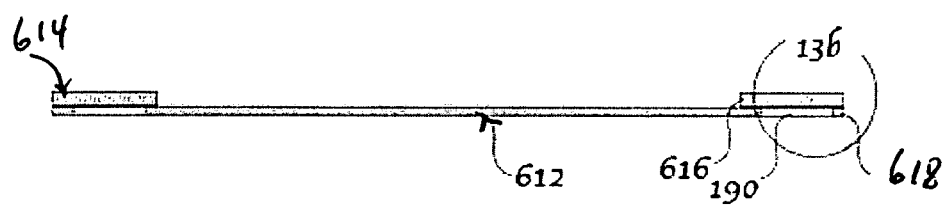
FIG. 13a is a cross-sectional view of the eyewear in FIG. 13 along line 13a-13a of FIG. 13.
Figure 13B:
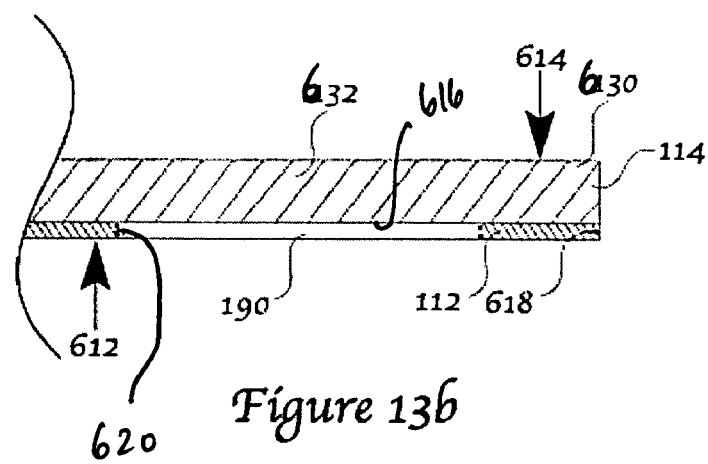
FIG. 13b is a partial, magnified cross section of a portion of the eyewear in FIG. 13.

FIGS. 13, 13a and 13b illustrate another embodiment of the present invention where the adhesive frame overlays a portion of the lens having a cut-out section adjacent a lateral section of the lens. The eyewear 610 comprises a lens 612 that extends laterally to cover the user's eyes during use. The lens 612 has lateral portions 190 each defining a knock-out or hole that are preferably disposed near the lateral edges of the lens 612. The portion 190 has a perimeter 620 that is disposed interior to the lens perimeter 618. The eyewear 610 also includes two frames 614 disposed adjacent opposed lateral sections of lens 612 and overlays lateral portions 190, which provide adhesive attachment to the lens 612 and a portion of the user's face during use. Although the design of this eyewear embodiment illustrates two adhesive frames, a plurality of frames could be used to provide attachment to the lens and/or the user's face. Each frame 614 has a first portion 630 and a second portion 632 that adhere, respectively, to the lens adjacent perimeter 620 and the lateral portions of the user's face, e.g., adjacent the cheekbone area of a user's face. Adhesive portion 632 provides adhesive attachment, preferably in a releasable fashion, through the hole defined by lateral portion 190.

A substantial portion of this eyewear embodiment remains open to the environment to allow for free passage of air between the lens 612 and the user's eyes. This allows for free air movement between the lens 612 and the user's face. The free exchange of air ensures that no fog will form on the inside of the lens 612. Lens 612 may include scorings (not shown) that provide better conformity of the eyewear to the contours of the user's face.

In FIG. 13b, frame 614 is shown overlaying lateral portion 190 defining the hole and adhesively attached to lens 612 along the lateral section of lens 612 adjacent perimeter 620. As shown in FIG. 13b, frame end 114 overlays lens end 112. Ends 112 and 114 need not line up exactly as illustrated. Frame 614 has an adhesive side that provides assembly of the eyewear 610 along a first portion 630 of frame 614 and adjacent perimeter 620. Further, the adhesive side 616 of frame 614 provides a means of adhesive attachment to the face of a user, preferably in a releasable manner, along a second portion 632 of frame 614 through the hole defined by portion 190. Irrespective of the means of construction of the eyewear, the frame should have an adhesive or tacky material along the second portion thereof to provide preferably releasable attachment to a wearer's face.

Figure 14:
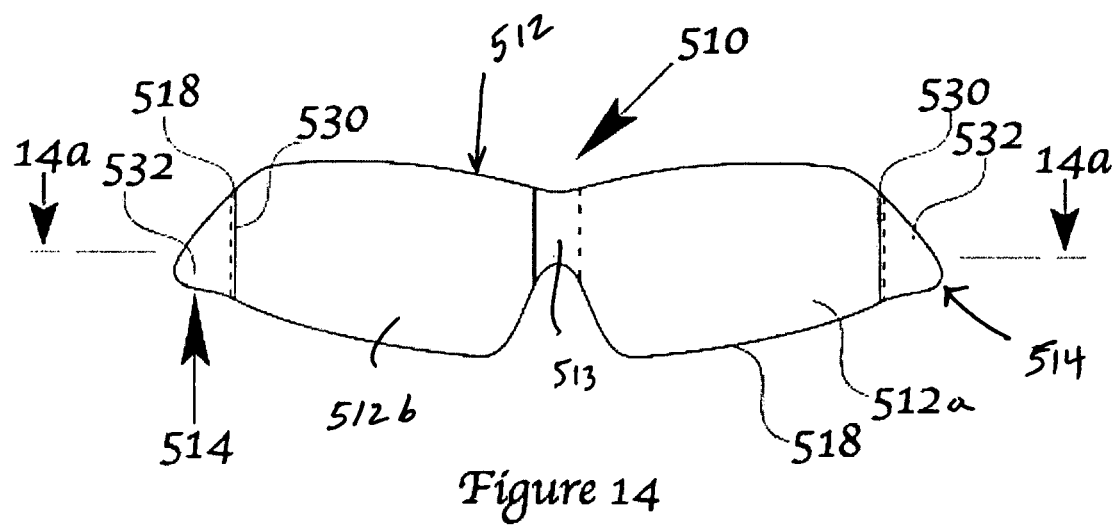
FIG. 14 is a plan view of another embodiment of eyewear according to the present invention.
Figure 14A:
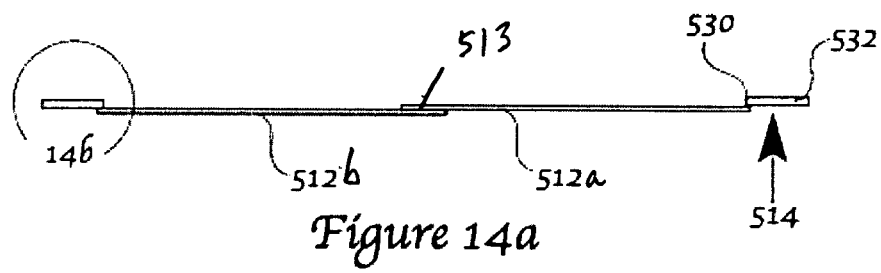
FIG. 14a is a cross-sectional view of the eyewear in FIG. 14 along line 14a-14a of FIG. 14.
Figure 14B:
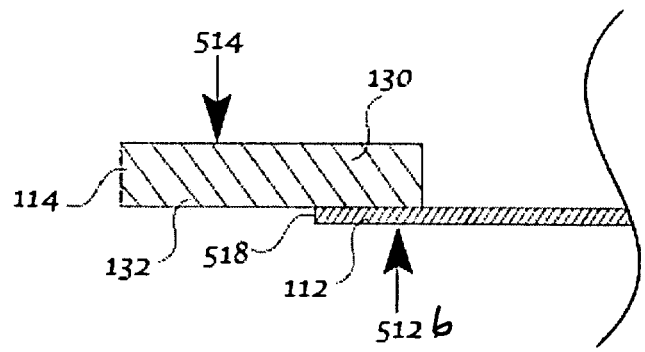
FIG. 14b is a partial, magnified cross section of a portion of the eyewear in FIG. 14.

FIGS. 14, 14a and 14b illustrate another embodiment of the present invention similar to the embodiment depicted in FIGS. 12, 12a and 12b, where the adhesive overlaps a non-continuous portion of the outside diameter of the perimeter along the lateral edges of the lens. However, FIG. 14 shows the lens comprising two distinct portions. The eyewear 510 comprises a lens 512 that extends laterally to cover the user's eyes during use. The lens 512 comprises two lens portions 512a and 512b that overlap along a center portion 513 of the lens. Thus, two distinct lens portions unite to form a unitary lens. The material making up the lens portions may comprise distinct materials or may comprise the same material that has been pigmented different colors. Such is the case where the eyewear is used for 3D viewing where one lens portion is tinted red and the other is tinted blue. The overlapping lens portions 512a and 512b may be bonded along center portion 513 using any of known mode of attachment or bonding, including using a double-stick adhesive to bond the two individual lens into one unit. Other suitable modes include laser bonding, melt bonding and pressure bonding.

The eyewear 510 includes two frames 514 disposed at opposed lateral edges of the perimeter 518 of lens 512, which provide adhesive attachment to the lens 512 and a portion of the user's face during use. Each frame 514 has a first portion 530 and a second portion 532 that adhere, respectively, to the lens along the lateral edge of the lens perimeter 518 and the lateral portions of the user's face, e.g., adjacent the temple area of a user's face. This allows for free air movement between the lens 512 and the user's face. In FIG. 14b, frame 514 is shown disposed adjacent lens portion 512b and adhesively attached thereto along a lateral edge of perimeter 518 of lens portion 512b. Frame end 114 overlays lens end 112 such that the frame end 114 extends beyond the lateral edge of perimeter 518 of lens portion 512b. Frame 514 has an adhesive side that provides assembly of the eyewear 510 along a first portion 130 of frame 514. Further, the adhesive side 516 of frame 514 provides a means of adhesive attachment to the face of a user, preferably in a releasable manner, along a second portion 132 of frame 514. The design of the frames may be of any shape and configuration provided it supplies a means of attachment to the lens and adhesive attachment (preferably in a easily releasable fashion) to the user's face.

Figure 15:
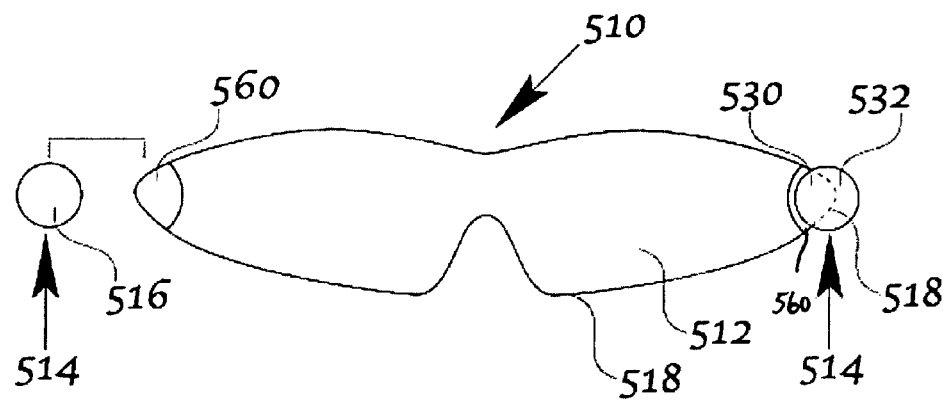
FIG. 15 is a plan view of another embodiment of eyewear according to the present invention showing in exploded fashion the components of eyewear in accordance with the present invention.

FIG. 15 illustrates a lens containing a release layer on a portion of the lens. Eyewear 510 includes a lens 512 incorporate opposed lateral portions 560 having releasable characteristics such that the adhesive of frame 514 that overlaps the lateral portion 560 can be removed from the lens and replaced. The lateral portions of the lens 560 may be treated with a chemical, compound or tape that provides a 'release' surface or release coating. The eyewear 510 includes two frames 514 disposed at opposed lateral edges of the lens 512, which provide adhesive attachment to the lens 512 and a portion of the user's face during use. Each frame 514 exhibits an adhesive side 516 that provides a means of adhesive attachment to the face of a user, preferably in a releasable manner, along a second portion 532 of frame 514, and has a first portion 530 and a second portion 532 that adhere, respectively, to the lens along the lateral portion of the lens 560 and the lateral portions of the user's face, e.g., adjacent the temple area of a user's face. This allows for free air movement between the lens 512 and the user's face. The lateral portions allow the wearer to easily remove the frame disc without damage to the lens or leaving behind some adhesive residue. Thus, the wearer can replace a used frame disc 514 with a new one and reuse the lens 512 repeatedly. Unlike the disposable (one-use) nature of other embodiments, this embodiment provides multiple uses of a single lens simply by using a plurality of replacement frames.

Figure 16:
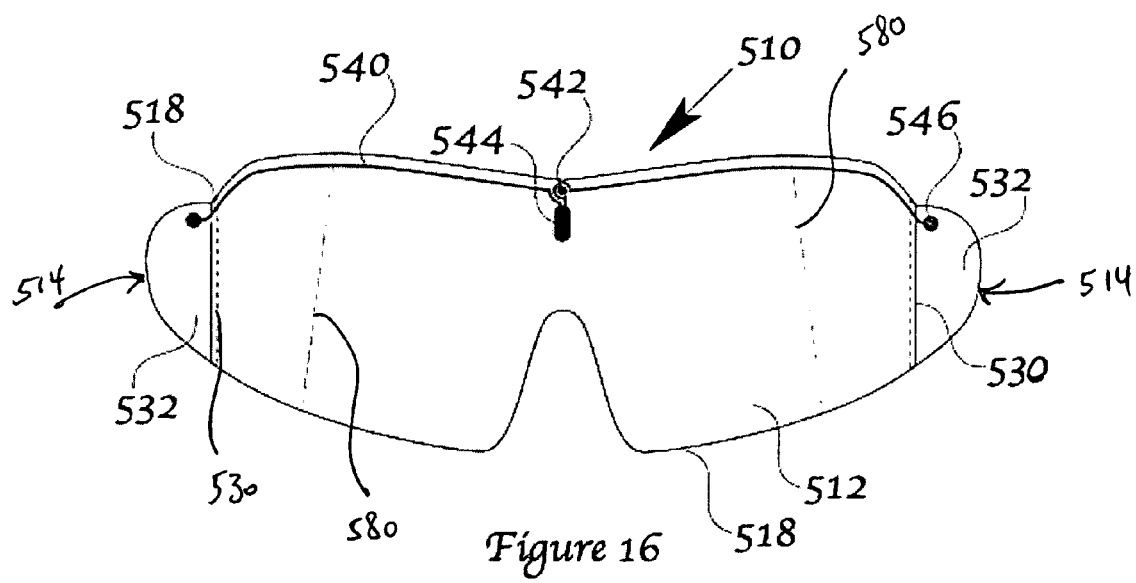
FIG. 16 is a plan view of yet another embodiment of eyewear according to the present invention.

FIG. 16 illustrates yet another preferred embodiment of the present invention. The eyewear 510 comprises a lens 512 and two frames 514 disposed at opposed lateral edges of the perimeter 518 of lens 512, which provide adhesive attachment to the lens 512 and a portion of the user's face during use. Each frame 514 has a first portion 530 and a second portion 532 that adhere, respectively, to the lens along the lateral edge of the lens perimeter 518 and the lateral portions of the user's face, e.g., adjacent the temple area of a user's face. Lens 512 includes scorings 580 that provide better conformity of the eyewear to the contours of the user's face.

Eyewear 510 in FIG. 16 incorporates a flat electrical circuit that is attached to the underside of the lens 512 and frames 514. There is a contact 546 on each frame that is disposed between the frame second portion 532 and the user's skin and contacting the user's skin during use. Eyewear 510 also includes a power source 544 and light source 542 that are integrated into the lens such that when it is worn by the user, the eyewear produces light to aid the wearer in dark settings. The contacts on the adhesive side of the frame complete the circuit when the user places the eyewear on their face. The electrical circuit is completed through the user's skin so that the light is on when the user is wearing the eyewear and off when it is not being worn. This is a disposable, single-use eyewear that provides limited light for a short period of time. The electrical circuit, power source and light source are well known to a person skilled in the art.

Figure 17:
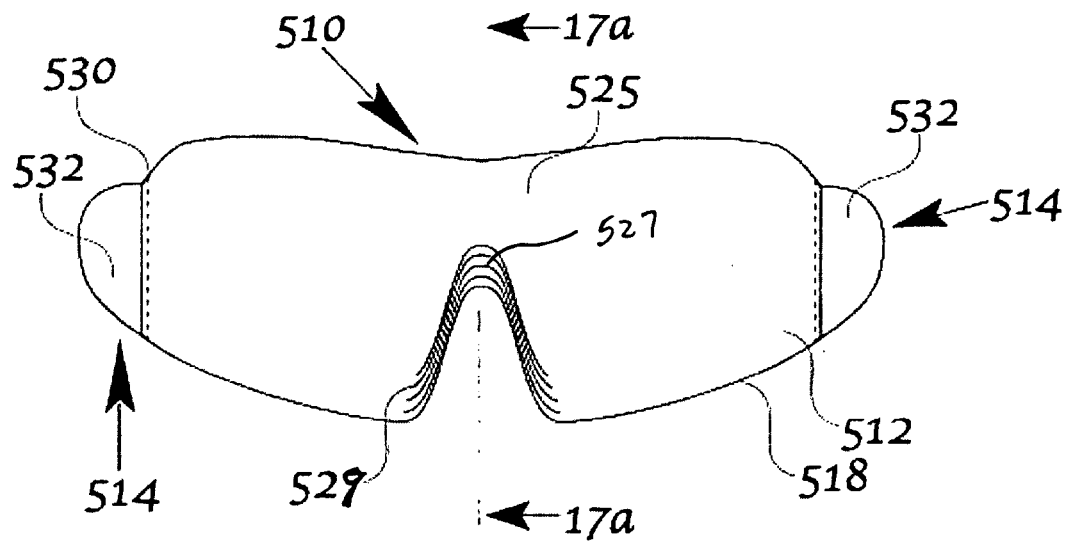
FIG. 17 is a plan view of an alternative embodiment of eyewear according to the present invention.
Figure 17A:
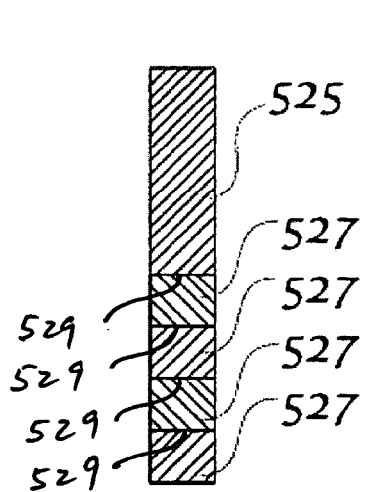
FIG. 17a is a cross-sectional view of the eyewear in FIG. 17 along line 17a-17a of FIG. 17.
Figure 17B:
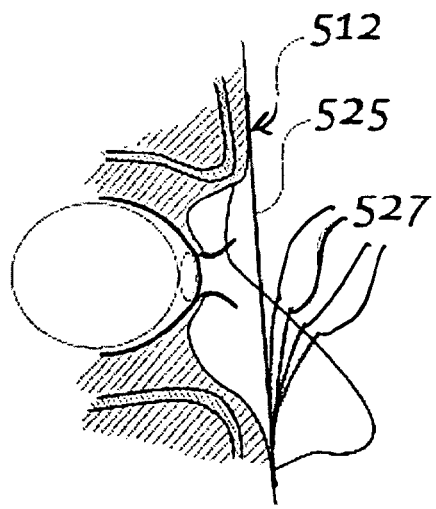
FIG. 17b is a pictorial cross section view of the eyewear in FIG. 17 as worn by a user.

FIGS. 17, 17a and 17b illustrate another embodiment of the present invention. The eyewear 510 comprises a lens 512 and two frames 514 disposed at opposed lateral edges of the perimeter 518 of lens 512, which provide adhesive attachment to the lens 512 and a portion of the user's face during use. Each frame 514 has a first portion 530 and a second portion 532 that adhere, respectively, to the lens along the lateral edge of the lens perimeter 518 and the lateral portions of the user's face, e.g., adjacent the temple area of a user's face. This eyewear embodiment incorporates a series of slits 529 adjacent a center portion 525 of the lens 512 along the area of the nose arch. Slits 527 define and form a plurality of gills 527 that conform to the shape of a wearer's nose. This allows the eyewear to better conform to the wearer's nose bringing the lens into a snug fit along the bridge of the nose and cheeks and provides added support across the bridge of the nose as the gills 527 comprising thin sections of the lens material spread out as the eyewear is placed onto the face.

Manufacturing Process

Materials

Sealing frame material is preferably a medical grade, plastic, conformable adhesive tape that is coated with a hypoallergenic, pressure sensitive adhesive. Exposed, non-adhesive side is capable of accepting printing for graphic and text treatments. The adhesive is applied during tape manufacture by the tape maker, such as 3M Corporation. In a preferred embodiment of the invention, frame material comprises a hypoallergenic material such as 3M Corporation's Medical Specialties Health care division's product number 1526, being a 3.6 mil thick, transparent, polyethylene film, coated on one side with a hypoallergenic pressure sensitive acrylate adhesive. The tape is supplied on a polyethylene coated, bleached Kraft paper liner, with a basis weight of 63 pounds, silicone coated one side, which has a nominal caliper of 4.9 mil. According to 3M product clinical data summaries for safety testing, the 1526 material has been subjected to suitable safety tests.

Lens material is preferably a plastic, semi-rigid, conformable, transparent material that can be clear or tinted. Lens material can be treated so that the interior will resist fogging as well as the exterior treated to reduce or eliminate the passage of ultraviolet light.

The assembled sealing frame and lens is mounted to a release backing 80, which is removed and disposed of by the wearer prior to placement on their face. The tape is supplied on a polyethylene coated, bleached Kraft paper liner, with a basis weight of 63 pounds, silicone coated one side, which has a nominal caliper of 4.9 mil.

The entire assembly is enclosed within a thin, waxed paper package (not shown) to protect the product during shipment.

Production Process

The sealing frame and lens materials can be cut to net shape using a CNC knife plotter or using a die cutting process, (hereinafter referred to generically as a cutting machine). In either case, the base material is supplied in rolls with pin-fed registration holes along each edge lengthways. The material is fed into the cutting machine at a controlled rate where multiple segments are cut progressively or simultaneously. Once cut the web or waste material is removed and disposed of or recycled. The lens and sealing frame components are assembled by placing the lens onto the sealing frame such that the adhesive on the sealing frame overlaps onto the lens border causing a bond between the materials; however, as described previously, the frame material extends laterally beyond the edge of the lens material to provide adhesive means for preferably releasable attachment to the wearer's face. Once assembled a release backing is applied, the finished assembly is then packaged for individual sale.

Construction means via converting the base materials, which are supplied in rolls are as follows. First slitting the base materials into nominal widths providing ample area to nest the finished shaped parts within. Net shape of the finished parts is achieved through automated rotary or steel rule die cutting operations where the lens is cut free from the base material web and the frame is kiss cut where the web is removed from the Kraft backing leaving the frame on the backing. Lens and frame are roll joined, printed, packaged and cut down into individual packages.

In an alternative process, a continuous coil of pre-layered materials is spooled and fed into a high-speed, rotary die cutting machine. The sunglass lens is sandwiched between the adhesive layer (TOP) and the release liner (BOTTOM). The die cutting operation can be optimized to use the minimal amount of release liner such that it only covers the adhesive layer with a slight overlap, under the lens that creates tabs for easy removal by the product user. During a single die stroke the adhesive and release liner is cut to follow the outer contour of the sunglass. The purpose of this is to reduce scrap, material costs as well as overall assembled product weight and thus freight costs. Depending upon the shipping requirements and the manufacturer's ability to protect the integrity of the lens in shipping, an additional, clear, "scratch sacrificial" layer can be added that adheres to the lens, which is removed just prior to use.

Additional Applications

The present invention has particular application to the medical field, industrial and sports and leisure industries, as described above. Those skilled in the art will recognize many other applications and uses including: Medical doctors, nurses, and hospital staff; Patients undergoing surgical, dental and other medical procedures; Dentists and dental technicians; Hospitals, nursing homes, and the like; Emergency medical technicians, firemen and police; Pharmacists; Laboratories; Electronics; Light industry; Painters; Carpenters and other construction personnel and the like; Beauticians; Janitorial workers; Visitor's and workers at hospitals; Visitor's and workers at factories; Personal protection when mowing lawns; Mechanics; Protects workers in food processing plants from wash down spray; Protection against agricultural and other sprays; Protection against small flying particles; Protection from fluid emersion and spray or splatter; Protection against light radiation and glare; Provides wearable fashion accessories; Provides means of sealing a fluid or gas against a wearers eyes or skin; Protection against laser light.

The invention claimed is:

1. Eyewear comprising:
a lens comprising opposed lateral edges, the lens adapted to cover a user's eyes; and
sealing frames disposed adjacent the opposed lateral edges, each sealing frame having an adhesive side, wherein each adhesive side comprises:
a first portion adapted to adhere the lateral edge to the frame; and
a second portion adapted to adhere the frame to at least a portion of a user's face, wherein, when adhered to a user's face, free air movement between the lens and a user's face and surrounding environment is allowed.

2. The eyewear as claimed in claim 1, wherein the frames each comprise a flexible, compliant material that is adapted to substantially conform to a user's face along the second portion and an adhesive material defining the adhesive of the frame.

3. The eyewear as claimed in claim 1, comprising more than one sealing frame at each lateral edge of the lens.

4. The eyewear as claimed in claim 1, wherein the lens comprises a flexible, transparent thermoplastic material.

5. The eyewear as claimed in claim 1, wherein the lens comprises at least one of a semi-rigid transparent material and a rigid transparent material and has a contour that substantially conforms to a shape and contours of a user's face adjacent a user's eyes.

6. The eyewear as claimed in claim 1, wherein the lens is coated with at least one of an anti-fogging coating, a UV protection coating, and a water-shedding coating.

7. The eyewear as claimed in claim 1, wherein the lens defines a notch defining a nose portion.

8. The eyewear as claimed in claim 1, wherein the second portion is adapted for forming a seal between the frames and at least a portion of a user's face adjacent the lateral edges of the lens.

9. Eyewear comprising:
a lens comprising:
opposed lateral edges adapted to cover a user's eyes; and
a first lens portion and a second lens portions that overlap along a central portion of the lens; and
sealing frames disposed adjacent opposed lateral edges of the lens, each sealing frame having an adhesive side, wherein each adhesive side comprises:
a first portion disposed along the lateral edges of the lens; and
a second portion extending beyond the lateral edges of the lens and adapted to substantially conform to a shape of a user's face such that, when adhered to a user's face, free air movement between the lens and a user's face and surrounding environment is allowed.

10. The eyewear as claimed in claim 9, wherein the frames each comprise a flexible, compliant material that is adapted to substantially conform to a user's face along the second portion and an adhesive material defining the adhesive side of the frame.

11. The eyewear as claimed in claim 9, comprising more than one sealing frame at each lateral edge of the lens.

12. The eyewear as claimed in claim 9, wherein the first and second lens portions each comprise at least one of a flexible transparent thermoplastic material, a rigid transparent thermoplastic material, and a semi-rigid transparent thermoplastic material, wherein the lens portions have differing colors or textures.

13. The eyewear as claimed in claim 9, wherein the lens has a contour that substantially conforms to a shape and contours of a user's face adjacent to a user's eyes.

14. The eyewear as claimed in claim 9, wherein the lens is coated with at least one of an anti-fogging coating, a UV protection coating, and a water-shedding coating.

15. The eyewear as claimed in claim 9, wherein the lens defines a notch defining a nose portion.

16. The eyewear as claimed in claim 9, wherein the second portion is adapted for forming a seal between the frames and at least a portion of a user's face adjacent to the lateral edges of the lens.

17. Eyewear comprising:
a lens comprising a perimeter and opposed portions each defining a hole adjacent lateral edges of the lens, the lens adapted to cover a user's eyes; and
sealing frames overlaying each of the opposed portions of the lens and having an adhesive side, wherein each adhesive side comprises:
a first portion adapted to adhere the frame to the lens and a second portion adapted to adhere the frame to at least a portion of a user's face, wherein, when adhered to a user's face, free air movement between the lens and a user's face and surrounding environment is allowable.

18. The eyewear as claimed in claim 17, wherein the frames each comprise a flexible, compliant material that is adapted to substantially conform to a user's face along the second portion and an adhesive material defining the adhesive side of the frame.

19. The eyewear as claimed in claim 17, wherein the lens comprises a flexible, transparent thermoplastic material.

20. The eyewear as claimed in claim 17, wherein the lens is coated with at least one of an anti-fogging coating, a UV protection coating, and a water-shedding coating.

* * * * *